Figure 1:
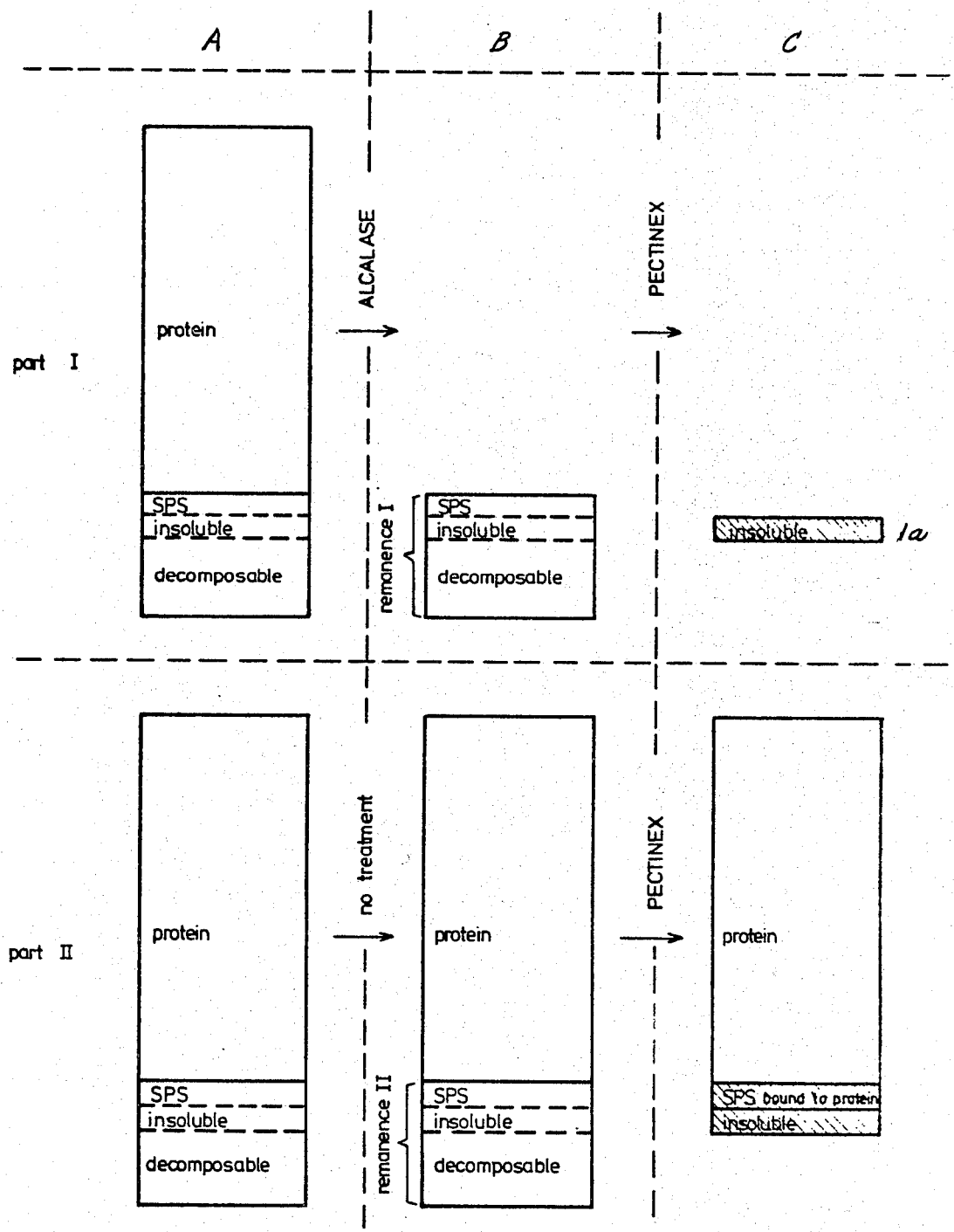

United States Patent [19]

Alder-Nissen et al.

[11] Patent Number: 4,478,940

[45] Date of Patent: Oct. 23, 1984

[54] PRODUCTION OF PURIFIED VEGETABLE PROTEIN

[75] Inventors: Jens L. Alder-Nissen, Gentofte; Henrick Gürtler, Lyngby; Georg W. Jensen, Bagsvaerd; Hans A. S. Olsen; Steen Riisgaard, both of Vaerlose; Martin Schülein, Copenhagen, all of Denmark

[73] Assignee: NOVO Industri A/S, Denmark

[21] Appl. No.: 334,330

[22] Filed: Dec. 24, 1981

[51] Int. Cl.³ .......................... C12N 9/24; C12N 9/40; C12N 9/42; C07G 17/00; A23J 1/14; A23L 2/34

[52] U.S. Cl. ..................................... 435/209; 435/200; 435/208; 435/274; 435/275; 435/262; 435/267; 435/272; 426/44; 426/46; 426/49; 426/51; 426/52

[58] Field of Search ................. 435/68, 262, 267, 272, 435/274–275, 200, 208, 209, 274, 275; 426/44, 46, 49, 51, 52

[56] References Cited

U.S. PATENT DOCUMENTS 3,484,255 12/1969 Okada et al. .................... 435/200 X
3,640,723 2/1972 Uhlig et al. ........................... 426/46
4,119,733 10/1978 Hsieh et al. ........................... 426/46

OTHER PUBLICATIONS

Kawai et al., Agricultural and Biological Chemistry vol. 43 (9) 1855–1862 (1979).
Research Disclosure 19314 May 1980.
Derwent Abstract 60536, C/35 (1980) of Belgian Pat. No. 882,769.

Primary Examiner—Lionel M. Shapiro
Attorney, Agent, or Firm—Fidelman, Wolffe & Waldron

[57] ABSTRACT

Purified vegetable protein particularly from soymeal produced by enzymatic treatment to dissolve the remanence employing a novel enzyme composition agent adapted to decompose a hitherto unreported pectic-like polysaccharide capable of binding to proteins.

4 Claims, 1 Drawing Figure

PRODUCTION OF PURIFIED VEGETABLE PROTEIN

This invention relates to improvements in enzyme composition agents for decomposition of vegetable remanence, especially soy remanence, methods for production of a purified vegetable protein product, and purified vegetable protein products.

INTRODUCTION

A method for production of a purified vegetable protein product (pvp) by enzymatic removal of the remanence, without dissolution and reprecipitation of the protein, is described in Belgian Pat. No. 882,769. Also, in this patent, the need to keep proteolytic activity in the enzyme as low as possible is described. The purity of the pvp obtainable by the known method is not satisfactory and, therefore, open to improvement. In the Examples provided by that Patent, a purity of the pvp of about 85% was demonstrated. Even if it is possible to obtain a pvp of about 90% purity according to the known method, such is only obtainable with certain pretreated starting materials, i.e., soy protein concentrate. It would be desirable to be able to obtain a purity of the pvp of above 90% with a much broader spectrum of starting materials, especially with dehulled and defatted soy meal.

The art has recognized that the remanence or non-protein (also non-starch, non-oil etc.) ingredients associated with vegetable materials like seeds, beans, nuts, etc., including soybeans, grape seeds, cotton seeds, sunflower seeds, faba beans, peas and peanuts constitutes a mixture containing the following polysaccharides:
 (1) Pectic-like polysaccharides mainly connsisting of D-galacturonic acid, D-galactose, L-arabinose, D-xylose, and L-rhamnose
 (2) Hemicelluloses
 (3) Cellulose However, even though vegetable materials, notably soy protein forms, have been treated with enzyme compositions containing pectinase, hemicellulase, and cellulase, a substantial proportion of the remanence has remained with the protein, which restated is advice that pvp of more than 90% protein has not been obtained heretofore.

RATIONALE OF THE INVENTION

The present invention is based upon the surprising discovery that a certain part of the remanence released from the vegetable matter substrate, e.g., soy meal, by the enzymatic action of carbohydrases is a hitherto unreported water soluble, pectic-like polysaccharide that does not separate from the vegetable protein. Presence of this polysaccharide is a principal reason for the relatively low protein content in pvp made with enzymatic treatment, i.e., pvp less than 90% for soy pvp.

Thus, an object of the invention is to provide an enzyme composition agent for decomposition of vegetable remanence, especially soy remanence, which will result in a pvp with improved purity, and to provide a method for production of a pvp.

The need for an enzyme composition agent containing a heretofore not recognized enzymatic ingredient can be seen from the following example.

EXAMPLE 1

A charge of soy meal was treated in aqueous suspension at pH 8 with Alcalase ® 0.6L (NOVO INDUSTRI A/S) a proteinase from *B. licheniformis*, for about four hours at 50° C., using one Anson Unit of enzyme per 100 gms of soy meal. The enzymatically degraded solubilized proteins were removed, leaving the remanence in solid form.

The remanence was then treated in aqueous suspension with a commercial pectinase (PECTINEX TM - NOVO INDUSTRI A/S) and the undissolved remanence portion (1a) removed and weighed.

A like charge of soy meal was treated only with the pectinase, which treatment left the protein in solid form, along with any remanence fractions not solubilized by the pectinase treatment. Analysis of the pectinase treated soy meal showed a polysaccharide content therein exceeding the undissolved remanence fraction (a).

When the carbohydrate containing supernatant remaining after pectinase treatment of the remanence and removal of the undissolved remanence fraction (1a) is brought together with a soy protein suspension, some polysaccharide disappears from the solution.

The results of the foregoing Example 1 can be described as follows with reference being made to the attached drawing whereon the results of Example 1 are shown; only materials existing as undissolved solids are indicated, all supernatants being left out. The total charge of soy meal divided in two equal parts, part I and part II (Column A in the drawing) is shown with Part I decomposed proteolytically at a pH value of about 8 by means of ALCALASE ® 0.6L. After washing at around pH 8 in order to eliminate the protein, the remanence was separated from the supernatant and washed. In this way, the pure remanence (designated Remanence I) was isolated (Column B, FIG. 1). For the sake of clarity, the remanence in Part II of the soy meal which was not treated has been designated Remanence II (Column B, FIG. 1). When Remanence I and all of Part II are decomposed by a commercial pectinase, e.g., PECTINEX TM, it is found that the undissolved part of Remanence I is much smaller than the undissolved part of Remanence II, on the basis of nitrogen and dry matter mass balances, vide FIG. 1, where the hatched areas in Column C correspond to the insoluble, non-protein materials.

That some discrete unusual fraction of the remanence has been solubilized by the treatment given Part I of the soy meal has been demonstrated (by bringing the supernatant from the pectinase treated Remanence I together with a soy protein suspension at pH 4.5, whereupon polysaccharide disappears from solution). This discrete polysaccharide fraction in the supernatant from Remanence I, i.e., the part of the remanence decomposition product, soluble in water in the absence of soy protein, but bound to soy protein at or around the isoelectric point of soy protein, if soy protein is present, has been designated SPS (Soluble Polysaccharide), vide FIG. 1.

The SPS has a molecular weight distribution between $5 \times 10^6$ and $4.9 \times 10^4$ and may be recovered by treating Remanence I with pectinase as described above, then subjecting the (supernatant) solution to ultrafiltration to remove oligosaccharides, leaving the SPS in the retentate. The SPS may, if desired, be precipitated from the retentate by addition of ethanol.

For detailed discussion of SPS itself and of enzymes capable of attacking SPS, i.e., an SPS-ase, reference is made to Ser. No. 339,329, concurrently filed herewith, the disclosure of which is incorporated herein by this reference thereto. Suffice it here for reasons of brevity to point out that SPS-ase is the enzyme capable of hydrolyzing SPS, i.e., the water soluble polysaccharide that binds to soy protein to an extent that the hydrolysis products of SPS lose capability to bind with soy protein.

The SPS-ase herein described have been produced from *Aspergillus aculeatus* CBS 101.43 and *Aspergillus japonicus* IFO 4408.

Also, the discussion hereinafter will for clarity, specifically refer to soy protein, but it should be appreciated that this invention is not restricted to treatment of soy material, but encompasses all kinds of vegetable materials, vide e.g., the protein containing materials listed in Belgian Pat. No. 882,769.

BRIEF STATEMENT OF THE INVENTION

Thus, the invention in its first aspect comprises an enzyme composition agent adapted to decompose vegetable remanence, especially soy remanence, in the presence of vegetable protein, especially soy protein, so as to produce a pvp with a protein purity of around 90% or more from a defatted vegetable material. The enzyme composition agent with remanence solubilizing activity includes, of course, an enzyme which is able to decompose SPS (SPS-ase), and little or no proteolytic activity. The proteinase activity in the agent is equal to or less than the proteolytic activity, which will be accompanied by a protein loss in the finished pvp of not more than 25% preferably not more than 15%, more preferably not more than 5%, when about 65% of the remanence has been solubilized. Inasmuch as the pvp is an excellent substrate for proteolysis, the present enzyme composition agent must be essentially free of proteolytic activity and a protein loss of less than 25% can be achieved only by an enzyme composition that is essentially free of proteolytic activity.

The invention comprises in its second aspect, a method for production of purified vegetable protein product by removal of the remanence from a vegetable protein containing starting material, wherein the starting material is treated with the enzyme composition agent according to this invention in an aqueous medium at a pH value which does not differ more than 1.5 pH units from the isoelectric point of the main part of the protein in the starting material, until at least about 60% of the remanence (based on nitrogen and dry matter mass balance), preferably at least about 65% thereof, more preferably at least about 75% thereof, has been solubilized, after which the solid phase containing the purified vegetable protein product is separated from the supernatant.

Treatment temperature should be in the range of 20° C.-70° C., preferably 40° C.-60° C. i.e., moderately elevated temperatures, but separation at 40° C.-60° C. causes a minor loss in pvp yield.

A preferred embodiment of the method of the invention is conduct of the separation at less than ambient temperature preferably nearer the freezing point than to ambient temperature. Thereby a higher protein yield is obtained.

a preferred embodiment of the method of the invention is characterized by use of starting material that is a defatted or a defatted and further partially purified vegetable protein. Such starting materials are readily available.

A preferred embodiment of the method according to the invention is characterized by use of soy meal as the starting material. This particular starting material is cheap and easily available. A preferred embodiment of the method according to the invention is characterized by use for the starting material of heat treated soy meal, preferably jet cooked soy meal. Thereby a lower enzyme dosage can be used, and furthermore, higher protein yield results.

A preferred embodiment of the method according to the invention is characterized by a starting material able to pass a sieve with a mesh opening of around 2.5 mm. This ensures a reasonably short reaction period.

The invention comprises in its third aspect a purified vegetable protein product, produced by the method according to the invention.

DISCUSSION OF THE INVENTION

By total or partial elimination of the SPS from the final vegetable protein the purity of the final vegetable protein necessarily is improved in comparison with the purity of the final vegetable protein obtainable according to the method known from Belgian Pat. No. 882,769, as this known vegetable protein product was contaminated with SPS.

The SPS-ase enzyme is an enzyme complex which derives its effect on SPS from pectolytic activity and SPS-activity. For detailed discussion on SPS-ase reference is made to companion application Ser. No. 339,329, filed concurrently herewith.

A preferred embodiment agent of the invention is the SPS-ase produced by a microorganism belonging to the genus Aspergillus, more preferably from the *Aspergillus niger* group.

A preferred embodiment agent of the invention is derived from the enzymes produced by *Aspergillus aculeatus* CBS 101.43. The SPS-ase is produced also by *Aspergillus japonicus* IFO 4408. It has been found that *Aspergillus japonicus* IFO 4408 and *Aspergillus aculeatus* CBS 101.43 also produce other very potent remanence solubilizing enzymes, namely cellulases, pectinases, and hemicellulases, with the latter microorganism productive of the greater yields.

Alluding now to the existence of many polysaccharides in remanence, it is, of course, evident that the enzyme composition agent herein contemplated will need contain many carbohydrase activities, notably SPS-ase, pectinase, cellulase and hemicellulase. Although unfractionated SPS-ase, such as the SPS-ase from *Aspergillus aculeatus* CBS 101.43 has other of the desired activities, by itself, the SPS-ase may not contain enough of the needed other activities to be the entirety of the enzyme composition agent herein contemplated. In practice of this invention a separate celluslase may form part of the agent.

Only the dosage rate (in SAE units) for the SPS-ase activity in treatment of soy meal can be provided. At least about 35 SAE units per 100 grams of jet cooked soy meal, and 350 SAE units per 100 grams of uncooked soy meal. As a practical matter, the exact interrelation of enzyme activities needed to degrade SPS is not known and, therefore, minimum dosages and proportions for pectinase celluslase and hemicellulase cannot be provided. However, a composite activity in treatment of soy meal in SRUM units can be provided, namely at least about 60 SRUM-120 units per 100 grams for cooked soy meal, 600 unheated meal. The exemplary values hereinafter provided are believed to be more than the minimum dosages. Cut and try tests may be employed to establish optimum operating proportions and reaction time for the soy substrate to be converted into pvp.

Reverting now to need for an enzyme composition agent essentially free of proteolytic activity, it is noted that attaining complete absence of proteolytic activity from SPS-ase has to date, also involved excessive loss in carbohydrase activity. But reduction of proteolytic activity to a very low level (still essentially free) has been feasible.

Some correlation between proteolytic activity and carbohydrase activity can be provided for one SPS-ase.

A preferred embodiment of the enzyme composition agent of the invention is characterized by a ratio between proteolytic activity in HUT-units and remanence solubilizing activity in SRUM-120units of less than about 2:1, preferably less than 1:1, more preferably less than 0.25:1. It has been found that correlation between the protease activity expressed in HUT units (defined hereinafter) at pH 3.2 and the protein loss exists. Unfortunately, the correlation appears to be specific for the SPS-ase preparation from *Aspergillus aculeatus* CBS 101.43, and this exact correlation may not exist in relation to SPS-ase from another SPS-ase forming microorganism. Cut and try tests may be needed to establish a comparable predictive correlation for minimizing protein loss.

The SRUM-120 activity (defined hereinafter) is a measure of the conventional remanence solubilizing, cellulase, pectinase, and hemicellulase, etc. activities. The SRUM-120 units are measured at pH 4.5, the isoelectric pH of the soy protein or at whatever pH the decomposition of the remanence is to be carried out.

If the SPS-ase (and/or the added cellulase) is found to contain excessive proteolytic activity, the enzyme or enzyme mixture may be treated to deactivate proteolytic activity.

In instances when cellulase is added to the SPS-ase a preferred embodiment agent of the invention is addition of cellulase activity derived from *Trichoderma reseei*, e.g., Celluclast TM (NOVO INDUSTRI A/S).

The SPS-ase elaborated by a preferred microorganism source is an enzyme mixture of SPS-ase activity, cellulase activity ($C_x$), pectinase activity (PU, PGE, UPTE, PEE) and hemicellulase activity (VHCU) as tabulated below.

TABLE 1.1

| Enzyme activity per g of enzyme composition | KRF 68 BII* | KRF 68 BIII* | KRF 92 BI* |
|---|---|---|---|
| SAE | | | |
| Plate test | + | + | + |
| Quantitative test | 301 | 349 | 430 |
| SRU | 507 | 481 | 757 |
| SRUM$_{120}$ | 1560 | 1720 | 1030 |
| HUT pH 3.2 | 105 | 339 | 397 |
| $C_x$ | 8044 | 9396 | 3092 |
| PU | 9000000 | 8800000 | 7600000 |
| PGE | 72000 | 77700 | 68800 |
| UPTE | 83700 | 76900 | 62400 |
| PEE | 910 | 770 | 790 |
| VHCU | 1100000 | 1000000 | 742000 |

*Preparations described in the companion application filed concurrently herewith.

The analytical methods are described in detail in the companion application.

EXAMPLES

For further understanding of this invention the following specific examples are presented.

EXAMPLE 2

This Example describes the production of a pvp from a dehulled and defatted soy flour, "Sojamel 13" (commercially available from Aarhus Oliefabrik A/S). The dry matter content of this flour was 94.0% and the protein content taken as (N×6.25) on a dry matter basis was 58.7%. The soy flour was treated with the SPS-ase preparation KRF 68 BII produced according to Example 1 of the related concurrently filed application, Ser. No. 339,329.

85.2 of the soy flour were suspended and kept stirred at 50° C. in 664.8 g of water, and pH was adjusted to 4.5 by means of 7.5 ml of 6 N HC1. 50 g of a solution containing 4.00 g of said SPS-ase preparation was added, and the reaction mixture was then agitated for 240 minutes at 50° C. The mixture was then cnetrifuged in a laboratory centrifuge (Beckman Model J-6B) for 15 minutes at 3000×g. The supernatant was weighed and analysed for Kjeldahl N and dry matter. The solid phase was then washed with a volume of water equivalent to the mass of supernatant obtained by the first centrifugation. This operation was performed twice. The solid phase was then freeze-dried, weighed and analysed for Kjeldahl N and dry matter (by an outside laboratory).

The results obtained in the experiment appear below in Table 2.1:

TABLE 2.1

| | RESULTS OBTAINED | | | | |
|---|---|---|---|---|---|
| | | | | Yields | |
| Component | Mass g | N × 6.25 % | Dry matter % | N × 6.25 | Dry matter |
| Soy flour | 85.2 | 55.2 | 94.0 | 100% | 100% |
| SPS-ase preparation | 4.00 | 75.6 | — | 6.4% | — |
| 1. Centrifugate | 666 | 1.50 | 5.04 | 21.2% | 42.0% |
| p.v.p. | 44.5 | 87.5 | 95.7 | 82.7% | 53.2% |

Thus, a p.v.p. was obtained with a protein purity, i.e. N×6.25 on dry matter basis, of 91.4%, and with a total yield of protein of 83%.

EXAMPLE 3

This example compares the protein yields, the nutritional quality and some functional properties of soy protein products made by the following three procedures:

A: The traditional isoelectric precipitation for production of soy protein isolate.

B: The traditional isoelectric wash for production of soy protein concentrate

C: The isoelectric wash with a remanence solubilizing enzyme for production of pvp.

In order to generate a true comparison of the process according to the invention (C) with the conventional soy protein processes (A and B) the same raw material was used throughout. Also, the study was conducted in such a manner that corresponding temperatures and treatment times are the same in all three cases. Only the pH-values were different due to the fundamental differences between the three experiments.

A. The traditional isoelectric precipitation for production of soy protein isolate.

425.8 g of soymeal (Sojamel 13) were extracted in 3574.2 g of tap water at 50° C. pH was adjusted to 8.0 with 20.1 g of 4 N NaOH. After stirring for 1 hour the slurry was centrifuged at 3000×g for 15 minutes using four one liter beakers in a laboratory centrifuge (Beckman Model J-6B). The centrifugate I and the precipitate I were weighed. The precipitate I was re-extracted with water to a total weight of 4000 g. The temperature was kept at 50° C., pH adjusted to 8 with 4 N NaOH and the slurry kept stirred for one hour. A centrifugation and weighing of centrifugate II and precipitate II were performed as above. Samples were drawn from centrifugate I and II and precipitate II for Kjeldahl and dry matter determinations. Hereafter the centrifugates I and II were mixed and held at 50° C. The protein was then isoelectrically precipitated by adjustment to pH 4.5 with 45 g of 6 N HCl. After stirring for 1 hour at 50° C. the protein was recovered by centrifugation at 3000×g for 15 minutes. The centrifugate III was weighed and analysed for Kjeldahl-N and dry matter. The solid phase III was weighed and washed with water in an amount corresponding to the weight of centrifugate I. The washing was carried out by stirring for one hour at 50° C. The washed protein was recovered by centrifugation at 3000×g for 15 minutes. The centrifugate IV and the solid phase IV were weighed. Centrifugate IV was analysed for Kjeldahl-N and dry matter. The solid phase was suspended in 1550 g of water at 50° C. and pH was adjusted to 6.5 with 17 g of 4 N NaOH. The mixture was kept stirred for one hour and re-adjusted to pH=6.5. Finally the product was freeze dried, weighed, and analysed for Kjeldahl-N and dry matter. The mass balance calculations are shown in table 3.1.

TABLE 3.1

Mass balance calculations of isoelectric precipitation for production of soy protein isolate.

| Operations and fractions | Mass of fraction g | Protein % (N × 6.25) | Dry matter % | Yield of protein, % | Yield of dry matter, % |
|---|---|---|---|---|---|
| Extraction: Soy flour | 425.8 | 55.2 | 94.0 | 100.0 | 100.0 |
| Water | 3574.2 | 0 | 0 | 0 | 0 |
| 4 N NaOH | 20.1 | 0 | 16.0 | 0 | 0.8 |
| 1. Centrifugation: Σ | 4020.1 | 5.9 | 10.0 | 100.9 | 100.4 |
| Centrifugate I | 3141.0 | 4.4 | 6.9 | 58.8 | 54.1 |
| Precipitate I | 805.0 | — | — | — | — |
| Re-extraction: | | | | | |
| Precipitate I | 805.0 | — | — | — | — |
| Water | 3195.0 | 0 | 0 | 0 | 0 |
| 2. Centrifugation: | | | | | |
| Centrifugate II | 3104.0 | 0.5 | 0.9 | 6.6 | 7.0 |
| Precipitate II | 820.0 | 9.1 | 17.2 | 31.7 | 35.2 |
| Mixing and acidifying: | | | | | |
| Centrifugates I + II | 6245.0 | — | — | — | — |
| 6 N HCl | 45.0 | 0 | 21.3 | 0 | 2.4 |
| 3. Centrifugation: Σ | 6290.0 | | | | |
| Centrifugate III | 5650.0 | 0.3 | 1.9 | 7.2 | 26.8 |
| Precipitate III | 308.0 | — | — | — | — |
| Washing: | | | | | |
| Precipitate III | 308.0 | — | — | — | — |
| Water | 3141.0 | 0 | 0 | 0 | 0 |
| 4. Centrifugation: Σ | 3449.0 | | | | |
| Centrifugate IV | 3113.0 | 0.04 | 0.15 | 0.5 | 1.2 |
| Precipitate IV | 291.0 | — | — | — | — |
| Neutralization: | | | | | |
| Precipitate IV | 291.0 | — | — | — | — |
| Water | 1550.0 | 0 | 0 | 0 | 0 |
| 4 N NaOH | 17.0 | 0 | 16.0 | 0 | 0.7 |
| Drying: Powder | 128.0 | 93.8 | 96.3 | 51.1 | 30.8 |

B. The isoelectric wash for production of soy protein concentrate 425.6 g of soy meal (Sojamel 13) was washed in 3574 g of water at 50° C. pH was adjusted to 4.5 with 44.8 g of 6 N HCl. The washing was carried out for four hours by agitating. The slurry was then centrifuged at 3000×g for 15 minutes in a laboratory centrifuge (Beckman Model J-6B) using four one liter beakers. The centrifugate I was weighed and analysed for Kjeldahl N and dry matter. The solid phase I was weighed and re-washed with water to a total weight of 4000 g. pH was re-adjusted to 4.5 with 1.7 g of 6 N HCl and the slurry was kept stirred for 30 minutes at 50° C. A centrifugation and weighing of centrifugate II and solids II were performed as above. The solid phase II was resuspended in 1575 g of H$_2$O at 50° C. and pH was adjusted to 6.5 with 34.5 g of 4 N NaOH. The mixture was kept stirred at 50° C. for one hour and re-adjusted to pH=6.5. Finally the protein product was freeze dried, weighed, and analysed for Kjeldahl N and dry matter. The mass balance is shown in table 3.2.

TABLE 3.2

Mass balance calculations of isoelectric wash for production of soy protein concentrate.

| Operations and fractions: | Mass of fraction g | Protein % (N × 6.25) | Dry matter % | Yield of protein, % | Yield of dry matter, % |
|---|---|---|---|---|---|
| Washing: | | | | | |
| Soy flour | 425.8 | 55.2 | 94.0 | 100.0 | 100.0 |
| Water | 3574.0 | 0 | 0 | 0 | 0 |
| 6 N HCl | 44.8 | 0 | 21.3 | 0 | 2.4 |
| 1. Centrifugation: Σ | 4044.6 | — | — | — | — |
| Centrifugate I | 3150.0 | 0.6 | 3.2 | 8.0 | 25.2 |
| Solids I | 846.0 | — | — | — | — |
| Re-washing: | | | | | |
| Solids I | 846.0 | — | — | — | — |
| Water | 3154.0 | 0 | 0 | 0 | 0 |
| 6 N HCl | 1.7 | 0 | 21.3 | 0 | 0.1 |
| 2. Centrifugation: Σ | 4001.7 | | | | |
| Centrifugate II | 3130.0 | 0.1 | 0.4 | 1.3 | 3.2 |
| Solids II | 863.0 | — | — | — | — |
| Neutralization: | | | | | |
| Solids II | 863.0 | — | — | — | — |
| Water | 1575.0 | 0 | 0 | 0 | 0 |
| 4 N NaOH | 34.5 | 0 | 16.0 | 0 | 1.4 |
| Drying: Powder | 281.0 | 72.5 | 98.4 | 86.7 | 69.1 |

C. The isoelectric wash with a remanence solubilizing enzyme for production of p.v.p.

425.8 g of soy meal (Sojamel 13) was washed in 3524.2 g of water at 50° C. pH was adjusted to 4.5 by 43.7 g of 6 N HCl. 24 g of the SPS-ase preparation KRF 68 BIII (example 1) were solubilized in 26 g of water and added to the washing mixture. The washing was then carried out for four hours, with agitation. Subsequently, the purification was performed as described above in B, the amounts of 6 N HCl, 4 N NaOH and water for resuspension being the only parameters with deviating values. The mass balance is shown in table 3.3.

TABLE 3.3

Mass balance calculations of isoelectric wash with a remanence solubilizing enzyme for production of p.v.p.

| Operations and fractions: | Mass of fraction g | Protein % (N × 6.25) | Dry matter % | Yield of protein, % | Yield of dry matter, % |
|---|---|---|---|---|---|
| Washing: | | | | | |
| Soy flour | 425.8 | 55.2 | 94.0 | 100.0 | 100.0 |
| Water | 3540.2 | 0 | 0 | 0 | 0 |
| 6 N HCl | 43.7 | 0 | 21.3 | 0 | 2.3 |
| SPS-ase: KRF 68 BIII | 24.0 | 75.3 | 96.0 | 7.7 | 5.8 |
| 1. Centrifugation: Σ | 4043.7 | — | — | — | — |
| Centrifugate I | 3420.0 | 1.7 | 5.2 | 24.7 | 44.4 |
| Solids I | 620.0 | — | — | — | — |
| Re-washing: | | | | | |
| Solids I | 620.0 | — | — | — | — |
| Water | 3380.0 | 0 | 0 | 0 | 0 |
| 6 N HCl | 1.3 | 0 | 21.3 | 0 | 0.1 |
| 2. Centrifugation: Σ | 4001.3 | | | | |
| Centrifugate II | 3400.0 | 0.2 | 0.6 | 2.9 | 5.1 |
| Solids II | 577.0 | — | — | — | — |
| Neutralization: | | | | | |
| Solids II | 577.0 | — | — | — | — |
| Water | 1700.0 | 0 | 0 | 0 | 0 |
| 4 N NaOH | 25.3 | 0 | 16.0 | 0 | 1.0 |
| Drying: Powder | 211.0 | 87.3[1] 86.9[2] | 96.7[1] 97.0[2] | 78.2 | 51.1 |

[1]Analyzed at outside laboratory.
[2]Analyzed at outside laboratory.

Nutritional Properties

The amino acid compositions of the three protein products are listed in table 3.4. The total content of essential amino acids, the chemical score and the essential amino acid index (EAAI) is calculated using the FAO reference pattern from 1957.

The trypsin inhibitor content of the three products was determined by A.O.C.S. (American Oil Chemist Society) tentative method Ba 12–75. The results are shown in table 3.5 which also includes the yields and the protein/dry matter ratio of the three products

TABLE 3.4

Amino acid composition and nutritional evaluation of the three protein products A, B, and C.

| Amino acid | A. Soy protein isolate g/16 g N | aas[1] | B. Soy protein concentrate g/16 g N | aas[1] | C. Soy protein isolate (p.v.p.) g/16 g N | aas[1] |
|---|---|---|---|---|---|---|
| Non-essential: | | | | | | |
| Aspartic acid | 12.4 | — | 11.3 | — | 11.9 | — |
| Serine | 4.62 | — | 4.69 | — | 4.81 | — |
| Glutamic acid | 21.3 | — | 18.2 | — | 17.7 | — |
| Proline | 6.07 | — | 5.19 | — | 4.76 | — |
| Glycine | 4.13 | — | 4.26 | — | 4.33 | — |
| Alanine | 3.54 | — | 4.27 | — | 4.55 | — |
| Histidine | 2.83 | — | 2.78 | — | 2.50 | — |
| Arginine | 8.09 | — | 7.57 | — | 7.04 | — |
| Essential: | | | | | | |
| Isoleucine | 4.87 | >100 | 4.97 | >100 | 5.19 | >100 |
| Leucine | 7.80 | >100 | 7.98 | >100 | 8.09 | >100 |
| Lysine | 6.24 | >100 | 6.09 | >100 | 5.57 | >100 |
| Phenylalanine | 5.47 | >100 } >100 | 5.35 | >100 } >100 | 5.17 | >100 } >100 |
| Tyrosine | 3.38 | >100 | 3.88 | >100 | 4.44 | >100 |
| Cystine | 1.29 | 64.5 } 56.4 | 1.32 | 66.0 } 60.2 | 1.44 | 72.0 } 65.5 |
| Methionine | 1.08 | 49.1 | 1.21 | 55.0 | 1.31 | 59.5 |
| Threonine | 3.10 | >100 | 3.60 | >100 | 3.97 | >100 |
| Tryptophan | 1.06 | 75.7 | 1.37 | 97.9 | 1.32 | 94.3 |
| Valine | 4.90 | >100 | 5.23 | >100 | 5.57 | >100 |
| % total content of essential amino acids | | 38.36 | | 41.31 | | 42.21 |
| Chemical score | | 56.4% | | 60.2% | | 65.5% |
| EAAI | | 86.7% | | 90.2% | | 91.3% |

[1] aas = amino acid score based on the FAO reference pattern (1957)

TABLE 3.5

Process characteristics and trypsin inhibitor content of the three protein products A, B, and C.

| | A. Soy protein isolate | B. Soy protein concentrate | C. Soy protein isolate (p.v.p.) |
|---|---|---|---|
| Process Characteristics | | | |
| Protein of dry matter | 97.4% | 73.7% | 90.0% |
| Protein yield | 51.1% | 86.7% | 78.2% |
| Trypsin inhibitors TUI/g product | 34,000 | 21,000 | 19,000 |
| TUI/g protein | 36,250 | 28,970 | 21,810 |

Functional Properties

Nitrogen solubility index (NSI) was determined in a 1% protein disperstion at pH = 7.0 in 0.2 M NaCl and in distilled water respectively. After stirring for 45 minutes with a magnetic stirrer the suspension was centrifuged at 4000×g for 30 minutes, and the supernatant was analysed for nitrogen. The nitrogen solubility was calculated as (soluble N%/total N%). The results of this evaluation on the three products are shown in table 3.6.

Emulsifying capacity was determined three times on each product by a slightly modified Swift titration. 4.0 g of (N ×6.25) of the product was blended in 250 ml of 0.5 M NaCl with a Sorval Omnimixer at low speed. 50 ml of the suspension were transferred to a glass blender jar and 50 ml of soy bean oil were added. Hereafter the total mixture was weighed. The oil-water mixture was then homogenized at 10,000 rpm with the jar in an ice-bath. A supplementary amount of soy bean oil was added at a rate of 0.3 ml per second until the emulsion collapsed. The total amount of oil added before the "end point" was found by weighing.

Emulsifying capacity was calculated as ml oil per gram protein (N×6.25). The density of the oil was taken as 0.9 g/ml.

The average results of the determination of emulsifying capacity on the three products are shown in table 3.6.

Whipping expansion was determined in a 3% protein solution at pH=6.5. 250 ml of the aqueous dispersion of the protein samples were whipped (at speed III) for 4 minutes in a Hobart mixer (model N-50) mounted with a wire whip. The whipping expansion was calculated according to the formula $$\text{Whipping expansion} = V - 250/250 \times 100\%,$$

where V = final whip volume in ml.

V was measured by refilling the mixer jar with water. Duplicates were performed for each of the three samples. The average results are shown in table 3.6.

Foam stability was determined as the ratio between the amount of foam left after draining for 30 minutes and the original amount of foam. A gram of foam produced by the method above was introduced into a plastic cylinder (diameter 7 cm, height 9 cm) having a wire net with a mesh size of 1 mm×1 mm. The cylinder was placed on a funnel on top of a glass cylinder and the weight (B) of drained liquid in the glass cylinder is determined. The foam stability FS is defined by the equation $$FS = (A - B)/A \times 100\%$$

The results of the determination is shown in table 3.6.

The gel strength is in this specification defined as the Brookfield viscosity measured by means of T-spindles on a Brookfield Helipath stand. The gels were made by heat treatment of 12% protein suspensions in 0.5 M NaCl. The heat treatment was performed in closed cans with a diameter of 7.3 cm and a height of 5.0 cm placed in a water bath maintained at 80° C. and 100° C. each for 30 minutes. The cans were cooled and thermostatted to 20° C. before they were opened and measured. The results of the measurements are shown in table 3.6.

TABLE 3.6

Functional properties of the three protein products A, B, and C.

| Functionality | A. Soy protein isolate | B. Soy protein concentrate | C. Soy protein isolate (p.v.p.) |
|---|---|---|---|
| % NSI in 0.2 M NaCl | 39.5 | 20.3 | 25.6 |
| % NSI in water | 53.9 | 25.1 | 28.6 |
| Emulsifying capacity: ml oil/g (N × 6.25) | 218 | 182 | 354 |
| Whipping expansion % | 120 | 120 | 340 |
| Foam stability % | 50 | 50 | 20 |
| Gel strength [poise] 80° C. (0.5 M NaCl) | 1.7 × 10$^3$ | 1.2 × 10$^4$ | 3.3 × 10$^2$ |
| 100° C. (0.5 M NaCl) | 2.0 × 10$^4$ | 4.0 × 10$^4$ | 1.3 × 10$^4$ |

EXAMPLE 4

A p.v.p. was produced according to the procedure described in example 3 C except that the cellulase activity was partially derived from *Trichoderma reseei*. The commercial cellulase preparation CELLUCLAST ™ (Novo Industri A/S) dustri A/S) was treated with base at low temperature in the following manner. The pH value of a 10% CELLUCLAST ™ solution in water was adjusted to 9.2 with NaOH, and the thus resulting solution was cooled to 5° C. After 1 hour at this pH and temperature the pH was re-adjusted to 4.7 with 20% acetic acid. This solution was held at 5° C. overnight and then sterile filtered. The filtrate was freeze dried. 4 g of the freeze dried product was added together with the SPS-ase preparation KRF 68 BIII (from Example 1 of the companion application). The two enzymes were solubilized in 172 g of water before addition to the washing mixture. The mass balance calculations of this example is shown in Table 4.1.

The experiment demonstrates that the BIII SPS-ase preparation already contains adequate cellulase activity since addition of CELLUCLAST ™ does not seem to effect the protein/dry matter ration. (Other SPS-ase preparations such as the KRF-92 listed in Table 1.1 contain less cellulase activity.)

TABLE 4.1

Mass balance calculations of the iso-electric wash with an SPS-ase preparation and CELLUCLAST ™ for production of p.v.p.

| Operations and fractions | Mass of fraction gram | Protein % (N × 6.25) | Dry matter % | Yield of protein % | Yield of dry matter % |
|---|---|---|---|---|---|
| Washing: | | | | | |
| Soy flour | 425.8 | 55.2 | 94.0 | 100.0 | 100.0 |
| Water | 3546.2 | 0 | 0 | 0 | 0 |
| 6 N HCl | 43.1 | 0 | 21.3 | 0 | 2.3 |
| SPS-ase: KRF-68-B-III | 24.0 | 75.3 | 96 | 7.7 | 5.8 |
| CELLUCLAST | 4.0 | 43.6 | 96 | 0.7 | 1.0 |
| Centrifugation: Σ | 4043.1 | — | — | — | — |
| Centrifugate I | 3382.0 | 1.9 | 5.5 | 27.3 | 46.5 |
| Solids I | 661.0 | — | — | — | — |
| Re-washing: | | | | | |
| Solids I | 661.0 | — | — | — | — |
| Water | 3339.0 | 0 | 0 | 0 | 0 |
| 6 N HCl | 0 | 0 | 0 | 0 | 0 |
| 2nd centrifugation: Σ | 4000.0 | | | | |
| Centrifugate II | 3414.0 | 0.2 | 0.7 | 2.9 | 6.0 |
| Solids | 582.0 | — | — | — | — |
| Neutralization: | | | | | |
| Solids II | 582.0 | — | — | — | — |
| Water | 1691.0 | 0 | 0 | 0 | 0 |
| 4 N NaOH | 25.3 | 0 | 16.0 | 0 | 1.0 |
| Drying: | 206.0 | 88.8 | 98.9 | 77.8 | 50.9 |
| Powder | | | | | |

EXAMPLE 5

A p.v.p. was produced according to the method described in example 3 C except that all quantities were scaled down by a factor of 5, and that the reaction mixture was cooled to about 5° C. prior to the centrifugation. On the basis of the analytical results in relation to the centrifugates the calculated yield of precipitated protein is shown in Table 5.1.

TABLE 5.1 protein yields obtained in the production of p.v.p.

| | | | | Example 3 C | |
|---|---|---|---|---|---|
| Fractions | Mass g | Protein (N × 6.25) % | Yield of protein % | Protein (N × 6.25) % | Yield of protein, % |
| Soy flour | 85.2 | 55.2 | 100 | 55.2 | 100 |
| SPS-ase KRF-68 B-III | 4.8 | 75.3 | 7.7 | 75.3 | 7.7 |
| 1st centrifugate | 639 | 0.99 | 13.5 | 1.7 | 24.7 |
| 2nd centrifugate | 595 | 0.13 | 1.6 | 0.2 | 2.9 |

TABLE 5.1-continued

| | | protein yields obtained in the production of p.v.p. | | | |
|---|---|---|---|---|---|
| | | | | Example 3 C | |
| Fractions | Mass g | Protein (N × 6.25) % | Yield of protein % | Protein (N × 6.25) % | Yield of protein, % |
| p.v.p. | — | 87.2[a] | 92.6[b] | 87.1 | 80.1[b] |

[a]Average of 87.5 and 86.9 dry matter is 97.6 and 98.0%, respectively.
[b]Calculated as total mass of protein − protein lost in centrifugates.

EXAMPLE 6

Demonstration of the protein binding of SPS 40 grams of (N×6.25) from a commercial soy protein isolate (Purina 500 E from Ralston Purina) was dissolved in 680 g of water. The mixture was heated in a water bath to 50° C., and pH was adjusted to 4.50 with 6 N HCl. 90 g of this mixture was transferred to 5×250 ml Erlenmeyer flasks, and 10 g of aqueous solutions containing respectively 0 g, 0.2 g, 0.4 g, 0.8 g, and 1.6 g of the SPS produced as described previously in this specification was added. The flasks were then held under stirring with a magnet in a water bath at 50° C. for 240 minutes.

Hereafter the slurries were centrifuged at 3000×G for 15 minutes, and the centrifugates I were analysed for Kjeldahl-N and dry matter. The solid phases were washed in water at room temperature and re-centrifuged. This procedure was repeated. Then the solids were dispersed in 50 ml of water, and pH was adjusted to 6.50 by drop-wise addition of 6 N NaOH. The neutralized products were freeze dried and analysed for Kjeldahl-N and dry matter. Based on the analysis shown in Table 6.1, the protein recovery and the percentage of SPS which has been bound to the protein are calculated by means of the formulas shown in relation to Table 6.2.

This example demonstrates that the SPS is bound firmly to the protein so that the protein/dry matter ratio decreases with increasing content of SPS. An SPS content comparable to about 0.4 g in 10 g of water added to 5 g of protein isolayte is the protein/SPS ratio present in the soy flour.

The % binding of SPS is a calculated value. The % binding of SPS decreases due to saturation of the protein with regard to SPS at the low protein/SPS ratios.

TABLE 6.1

| | Measurements | | | | | |
|---|---|---|---|---|---|---|
| | Centrifugates I | | Dried precipitate | | | |
| Ratio Protein/SPS | % N | % DM | % N | % N × 6.25 | % DM | % $\frac{N \times 6.25}{DM}$ |
| ∞ | 0.068 | 0.62 | 13.2 | 82.5 | 93.1 | 88.6 |
| 25 | 0.045 | 0.49 | 13.4 | 83.8 | 97.3 | 86.1 |
| 12.5 | 0.038 | 0.45 | 13.0 | 81.3 | 97.9 | 83.0 |
| 6.25 | 0.031 | 0.45 | 12.6 | 78.8 | 98.1 | 80.3 |
| 3.125 | 0.026 | 0.61 | 11.8 | 73.8 | 97.9 | 75.3 |

TABLE 6.2

| Protein recovery and % binding of SPS | | |
|---|---|---|
| Ratio Protein/SPS | % recovery of protein[1] | % binding of SPS[2] |
| ∞ | 91.5 | 0 |
| 25 | 94.4 | 77 |
| 12.5 | 95.3 | 90 |
| 6.25 | 96.1 | 70 |

TABLE 6.2-continued

| Protein recovery and % binding of SPS | | |
|---|---|---|
| Ratio Protein/SPS | % recovery of protein[1] | % binding of SPS[2] |
| 3.125 | 96.8 | 60 |

[1]% recovery of protein = $\left[ 1 - \frac{NC\ 1 \times 6.25}{5} \right] \times 100$, where NC 1 = % N in centrifugate I
[2]% binding of SPS =

$$\frac{\frac{5 \times (\% \text{ recovery of protein})}{(\% \text{ P/H})} - \frac{5 \times (\% \text{ recovery of protein})}{(\% \text{ P/H})_\infty}}{[5/\text{ratio of SPS}]} \times 100,$$

where (% P/H) is the protein/dry matter ratio in the dried precipitate, and (% P/H) ∞ is for the precipitate without addition of SPS.

EXAMPLE 7

This example describes the production of a p.v.p. using the SPS-ase preparation KRF 92 B-I in a dosage of 5% of the dry matter. The manner of production was exactly as in Example 3 C, except that all quantities were scaled down by a factor of 5. The pvp was analysed as described in Example 2. The results obtained in the experiment appear from Table 7.1.

TABLE 7.1

| Component | Mass g | (N × 6.25) % | Dry matter % | Yield of protein, % | Yield of dry matter, % |
|---|---|---|---|---|---|
| Soy flour | 85.2 | 55.2 | 94.0 | 100 | 100 |
| Enzyme preparation | 4.0 | 71.2 | — | 6.1 | — |
| 1st centrifugate | 632 | 1.88 | 5.44 | 25.3 | 43.0 |
| 2nd centrifugate | 673 | 0.30 | 0.80 | 4.3 | 6.7 |
| p.v.p. | 39.8 | 85.6[a] | 98.1[a] | 71.9 | 48.8 |
| | | 84.4[b] | 98.1[b] | | |

[a]Analyzed by outside laboratory
[b]Analyzed by outside laboratory

EXAMPLE 8

This example demonstrates the effect of pretreating the soy meal by jet cooking before the production of p.v.p.

Pretreatment

A slurry of soymeal in water consisting of 10 kg soymeal (Sojamel 13) per 100 kg was pumped through a steam-ejector (type Hydroheater B-300) and mixed with enough steam of 8 Bar so a final temperature of 150° C. could be maintained for 25 seconds in a tubular pressurized reactor. Then the pressure was released in a flash chamber (a cyclone) and from here the slurry was sent through a plate heat exchanger and cooled to about 50° C. The cooled slurry could be used directly for production of p.v.p. by the method of the present invention, but in this instance, the slurry was spray-dried at an inlet temperature of 200° C. and at an outlet temperature of 90° C. The pretreated product was found to have a dry matter content of 96.5% and a protein content of 56.9% (N×6.25).

Production of p.v.p.

This production was carried out in the following way:

70 g of dry matter of the jet cooked and dried soy flour was suspended and stirred at 50° C. in 560 g of water, and pH was adjusted to 4.50 by 6.5 ml of 6NHCl. 6×90 g of this suspension was transferred to (six) 250 ml Erlenmeyer flasks and stirred on a 50° C. water bath by magnetic stirrers. To each flask were added 10 g of a solution containing respectively 0 g; 0.025 g; 0.050 g; 0.10 g; 0.20 g, and 0.40 g of the SPS-ase preparation KRF-68-B-III. The reaction mixtures were then agitated for 240 minutes at 50° C. Then a centrifugation at 300×g for 15 minutes was carried out. The supernatant was then analysed for Kjeldajl-N and the solid phase was washed with water at equal volumes and centrifuged. This procedure was performed twice. The solid phase was then freeze-dried and anlysed for Kjeldahl-N and dry matter.

A similar experiment was carried out with an untreated soy meal (Sojamel 13) as a starting material. In this case the enzyme substrate ratios were 0; 1%; 2%; 3%; 4%; and 8%.

Based on the protein content of the supernatants the percentage of recovered protein can be calculated. The yield of protein is based on the assumption that the enzyme product is 100% solubilized after the reaction. Table 8.1 shows the results obtained.

TABLE 8.1

| E/S % | Cooked soymeal | | Untreated soymeal | |
|---|---|---|---|---|
| | Protein yield % | Protein of dry matter % | Protein yield % | Protein of dry matter % |
| 0 | 92.9 | 76.5 | 90.7 | 73.9 |
| 0.25 | 90.1 | 86.6 | — | — |
| 0.50 | 89.3 | 88.7 | — | — |
| 1.0 | 88.1 | 89.7 | 87.1 | 86.2 |
| 2.0 | 86.6 | 91.7 | 85.7 | 88.1 |
| 3.0 | — | — | 84.3 | 89.5 |
| 4.0 | 84.7 | 92.2 | 82.6 | 90.9 |
| 8.0 | — | — | 76.2 | 91.1 |

We claim:

1. An enzyme composition agent adapted to degrade and solubilize polysaccharides in vegetable materials comprising SPS-ase, an enzyme capable of degrading the water soluble polysaccharide which binds to soy protein, said enzyme composition being further characterized by being essentially free from proteolytic activity, and by presence therein of activity against cellulose, pectin and hemicellulose in addition to SPS.

2. An agent according to claim 1, wherein the SPS-ase was produced by *Aspergillus aculeatus* CBS 101.43.

3. An agent according to claim 1, wherein the ratio between the proteolytic activity in HUT-units and the remanence solubilizing activity in SRUM-120 units is less than 0.25:1.

4. An agent according to claim 1, wherein the celluse activity in said composition comprises at least in part the cellulase of *Trichoderma reseei*.

* * * * *

UNITED STATES PATENT AND TRADEMARK OFFICE
CERTIFICATE OF CORRECTION

PATENT NO. : 4,478,940

DATED : Oct. 23, 1984

INVENTOR(S) : JENS L. ADLER-NISSEN et al.

It is certified that error appears in the above–identified patent and that said Letters Patent are hereby corrected as shown below:

Title page:

In [75] Inventors: "Jens L. Alder-Nissen"

should read --Jens L. Adler-Nissen--

Signed and Sealed this

Nineteenth Day of March 1985

[SEAL]

Attest:

DONALD J. QUIGG

Attesting Officer

Acting Commissioner of Patents and Trademarks